United States Patent [19]
Foerster et al.

[11] Patent Number: 5,271,415
[45] Date of Patent: Dec. 21, 1993

[54] GUIDEWIRE EXTENSION SYSTEM

[75] Inventors: Seth Foerster, Irvine; Sheryl Higgins, Silverado, both of Calif.

[73] Assignee: Baxter International Inc., Deerfield, Ill.

[21] Appl. No.: 826,707

[22] Filed: Jan. 28, 1992

[51] Int. Cl.$^5$ .............................................. A61B 5/00
[52] U.S. Cl. .................................. 128/772; 128/657
[58] Field of Search .................. 128/657, 772; 604/95, 604/164, 280–283; 403/43

[56] References Cited

U.S. PATENT DOCUMENTS

| | | |
|---|---|---|
| 862,082 | 7/1907 | Lewis . |
| 1,979,304 | 11/1934 | Anderson ............................ 403/43 |
| 2,276,571 | 3/1942 | Grypma ............................. 174/90 |
| 3,631,848 | 1/1972 | Muller ......................... 128/2.05 R |
| 4,616,648 | 10/1986 | Simpson ....................... 128/303 R |
| 4,827,941 | 5/1989 | Taylor et al. ....................... 128/657 |
| 4,846,193 | 7/1989 | Tremulis et al. .................... 128/772 |
| 4,875,489 | 10/1989 | Messner et al. .................... 128/772 |
| 4,907,332 | 3/1990 | Christian et al. .................... 29/237 |
| 4,917,103 | 4/1990 | Gambale et al. .................... 128/772 |
| 4,922,923 | 5/1990 | Gambale et al. .................... 128/772 |
| 4,966,163 | 10/1990 | Kraus et al. ....................... 128/772 |
| 5,031,636 | 7/1991 | Gambale et al. .................... 128/772 |
| 5,035,686 | 7/1991 | Crittenden et al. ................... 604/96 |
| 5,109,867 | 5/1992 | Twyford ........................... 128/657 |
| 5,113,872 | 5/1992 | Jahrmarkt et al. .................. 128/657 |
| 5,117,838 | 6/1992 | Palmer et al. ...................... 128/772 |

FOREIGN PATENT DOCUMENTS

| | | |
|---|---|---|
| 20155226 | 10/1990 | Canada . |
| 0347035 | 12/1989 | European Pat. Off. . |
| 0383159 | 8/1990 | European Pat. Off. . |
| 2745978 | 4/1979 | Fed. Rep. of Germany . |
| 2180454 | 6/1986 | United Kingdom . |

OTHER PUBLICATIONS

Article entitled "Guide Wire Extension" by Constantin Cope, M.D., published in Radiology 1985; 157:263.

*Primary Examiner*—Max Hindenburg
*Attorney, Agent, or Firm*—Kurt MacLean; Michael Schiffer; Raymond Sun

[57] ABSTRACT

A guidewire extension system is disclosed for connecting an extension wire to a guidewire having a tubular outer body, a guidewire retention element, an extension wire retention element, a guidewire and an extension wire. The guidewire retention element and the extension wire retention element are fixed within the outer body and are preferably helically wound wires which form a right-handed groove and a left-handed groove. The guidewire and the extension wire each have tapered ends and a reduced diameter extension core each having a helically wound wire formed to adhere to the extension core. The guidewire is connected to the extension wire by inserting the extension core of the guidewire into the outer tube and inserting the helically wound wire into the right-handed groove and by inserting the extension core of the extension wire into the outer tube and inserting the helically wound wire into the left-handed groove. The outer body is then rotated clockwise to simultaneously pull the extension wire and guidewire together until the tapers of each abut and bear against the outside edge of the outer tube providing a mechanical lock and providing a connection having the same pushability and flexibility as the guidewire. The system provides an extension wire to be connected to a guidewire without rotating the extension wire or the guidewire and provides for a unitized system that has a smooth, outer diameter of the extension wire, guidewire and outer body.

41 Claims, 1 Drawing Sheet

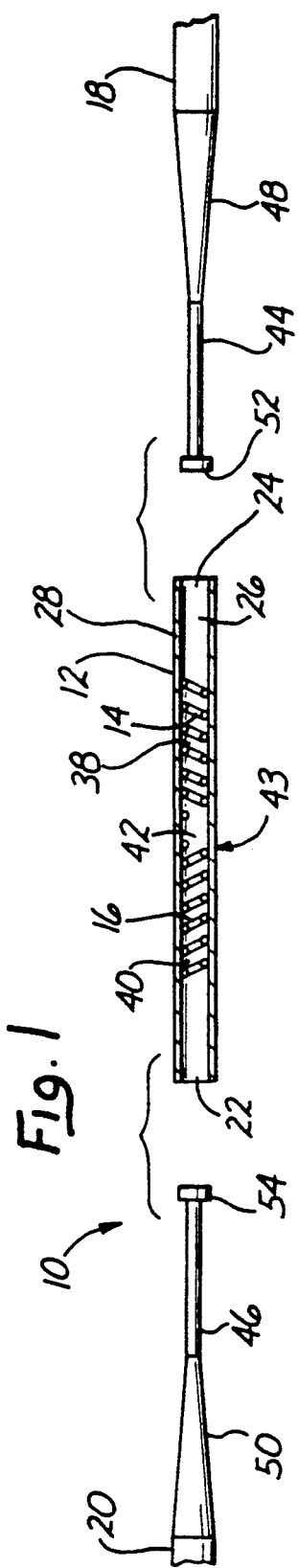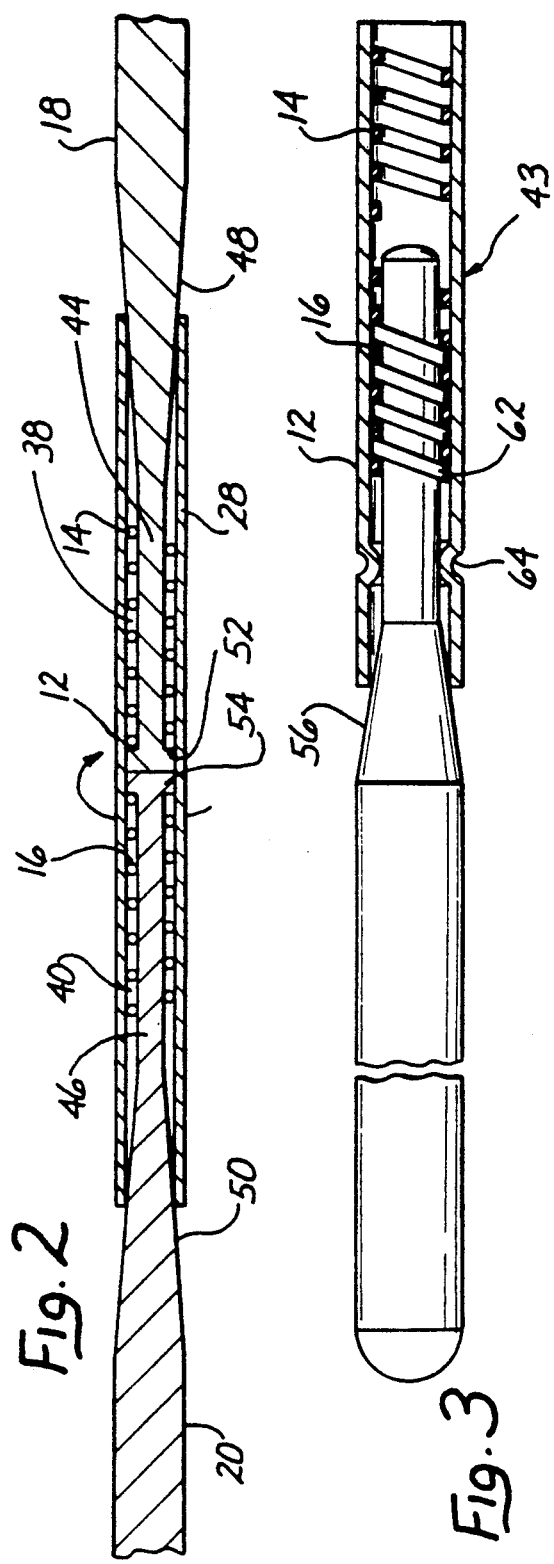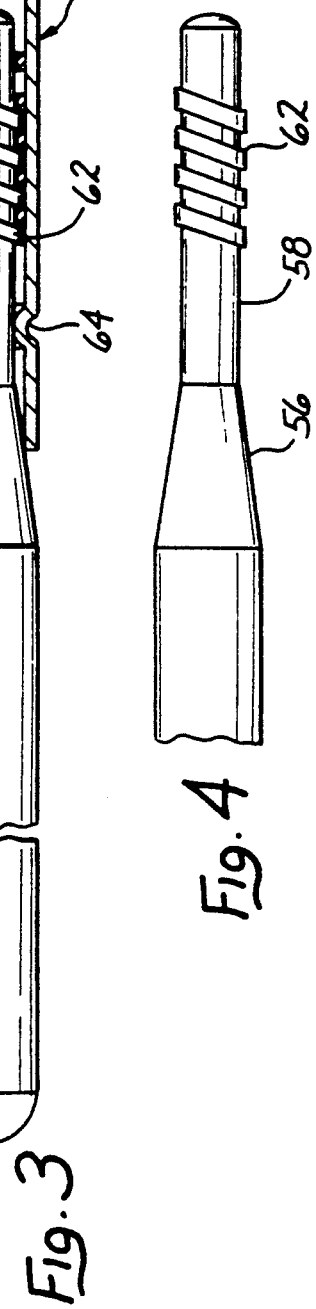

GUIDEWIRE EXTENSION SYSTEM

FIELD OF THE INVENTION

The present invention relates in general to the field of guidewire systems for use in guiding catheters in exploratory procedures, diagnosis and treatment of biological conditions, and more particularly, to a guidewire extension system for connecting a guidewire to an extension wire.

BACKGROUND OF THE INVENTION

Guidewires are used in various surgical procedures to pilot a device to a desired location in a patient's vascular system. Guidewires, in being a steerable device, are, generally, inserted and maneuvered through the patient's vasculature to a desired location. Once in place, the guidewire provides the means to place a steerless device, such as a catheter, at a chosen site in the patient's vasculature. Guidewires of a standard length are longer than the steerless device to allow for independent movement of the device and the wire.

In balloon angioplasty, one particular surgical application where a guidewire is used, the guidewire is maneuvered to an acute restriction in the patient's cardiovasculature. The piloting of the guidewire is facilitated by a video X-ray device allowing the surgeon to visually observe the movement of the guidewire's distal tip, made of a heavy metal to enhance X-ray viewing.

During a simple angioplasty, the balloon is inflated to open the restriction and then removed along with the guidewire. However, complications do arise which prevent the surgeon from completing this procedure. Sometimes the balloon catheter malfunctions, a larger balloon is required to further dilate the vascular restriction, another device is needed to remove vascular material, etc. The nature of the complication addressed by this invention requires the catheter, or other device, be removed to facilitate placement of another device. In such a situation, the device must be removed and another placed with the assistance of a guidewire.

It is desirable to keep the guidewire in the patient for various reasons. The initial placement of the guidewire requires extensive, time consuming manipulation. Removal and repositioning of the guidewire is equally time consuming requiring additional exposure to drugs, exposure of the patient to additional radiation, and the infliction of additional trauma to the patient.

In those cases where catheter exchange is desired, the surgeon removes the catheter over the guidewire, retaining the guidewire in the patient. To facilitate the removal and replacement of the catheters, the guidewire must be sufficiently long to allow the surgeon to grip a portion of the wire as the catheter is being withdrawn. This requires that the guidewire be long enough to provide an external portion longer than the catheter. However, a guidewire of such length has inferior handling characteristics adding significant difficulty to steering and maneuvering related manipulations. The added length also imposes itself on a usually cramped operating environment causing distractions to other surgical support activities. It is for this reason that guidewires are usually only slightly longer than the typical balloon catheter, e.g. 20–50 centimeters. In one previous method of catheter exchange, the original guidewire is replaced with a longer guidewire, after which the catheter is exchanged. This approach proved to be tedious.

A more recent development involves coupling a second length of wire to the exposed, proximal guidewire end. The second wire length should be of sufficient length to allow the catheter to be withdrawn while retaining the guidewire in the patient. Various approaches have been suggested for effecting the attachment of this added length.

In one approach, two wires are joined together by crimping which requires a special tool. Once the wires have been crimped, the connection therebetween is permanent, and the extension wire cannot be removed except by severing it from the guidewire. Instead of crimping, some attempts have tried to frictionally engage the extension wire to the guidewire. While frictional engagement overcomes the need to crimp, disengagement may still occur. Moreover, prior extendable wires for use in coronary angioplasty procedures have been found to be unsuitable in peripheral arteries because the connections are not strong enough and may disengage.

In another approach, the extension wire is twisted onto the guidewire. This requires that the entire wire be twisted. This can be cumbersome due to the length of the wire.

In still another approach, the guidewire is threaded into a bolt which is attached to the extension wire by means of a ball and socket swivel mechanism. The extension or guidewire do not need to be rotated to effect an attachment. The ball and socket mechanism, however, sacrifices pushability and flexibility as the ball and socket joint do not effect a mechanical lock sufficient to transmit such desirable properties.

Further, some connections are made at larger diameters than the rest of the guidewire system which may cause snagging of the catheter. A guidewire system having varying diameters requires a catheter, which is being passed over the guidewire, to have a larger internal diameter than would be necessary to fit over the smaller guidewire diameter.

Accordingly, a principal object of the present invention is to provide a guidewire extension system which is easy to use and easy to manufacture. It is a further object of the present invention to provide a guidewire extension system which minimizes the possibility of system failure by kinking or undesirable bending at the connection between the guidewire and the extension wire. Another object of the present invention is to provide a guidewire extension system utilizing a turnbuckle configuration which does not require that either the guidewire or extension wire be twisted. It is advantageous that the guidewire be held stationary because the guidewire is located within the patient's blood vessel where movement induces trauma. It is also advantageous to have the extension wire stationary and partially coiled in its package. Having the extension wire self-contained allows the operator to concentrate on engaging the two wires, whereas an unpackaged extension wire is awkward requiring additional attention thus complicating the logistics involved in effecting a union.

It is still a further object of the present invention to provide a guidewire extension system which has substantially the same flexibility and pushability at the connection as results with the standard guidewire.

Another object of the present invention is to provide a guidewire extension system using a threaded-type engagement such as that which results from applying helically twisted wires and a tube to fashion a turnbuckle nut. Such a turnbuckle nut provides a simple design to manufacture.

A further object of one embodiment of the present invention is to provide a guidewire extension system having bolt elements on the guidewire and on the extension wire which avoids the necessity of machining threaded bolts at the end of the guidewire and extension wire affording a simple design to manufacture.

It is yet another object of the present invention to provide a unitized guidewire extension system having a uniform, smooth, continuous outer diameter along the guidewire, connector, and extension wire.

SUMMARY OF THE INVENTION

In accordance with the present invention, a guidewire extension system is provided which is easy to manipulate, minimizes any possible failure at a connection point, and is easy to manufacture. The foregoing objectives are achieved through the use of an extension system connector having a body with at least one element for connecting the extension to the guidewire whereby the resulting connection has approximately the same pushability and flexibility as the guidewire. In one preferred form of the invention, the connection is made through threaded elements in a connector formed by a left-handed helically wound wire and a right-handed helically wound wire in the connector, whereby the guidewire and the extension wire threadably engage the threaded connector. The guidewire and extension wire are preferably pulled together by twisting only the connector without twisting the guidewire and extension wires.

In one preferred embodiment, a right-handed helically wound wire is brazed to the interior of a tubular outer body defining a helical groove along the inside wall of the outer body. A left-handed helically wound wire is also brazed to the interior of the tubular outer body to also define a helical groove along the inside wall of the outer body. The combination of the outer body and the helically twisted wires within form a turnbuckle nut. The helically wound wires are fixed within the outer body so that they are set back, preferably, from the respective ends of the outer body to accommodate an increasing taper on the extension and guidewires for the purpose of mechanically securing the wires to the turnbuckle. When the guidewire and extension wire are threaded within the turnbuckle, the ends of the turnbuckle bears against the tapered ends of the guidewire and extension wire so that the frictional contact forms a stable connection having substantially the same pushability and flexibility as the guidewire. The nature of this mechanical interface minimizes, preferably, the possibility of introducing adverse handling characteristics. Preferably, the turnbuckle nut connects the guidewire to the extension wire without having to rotate the guidewire or the extension wire.

The ends of the guidewire and the extension wire have connection ends. In one preferred embodiment, the connection ends of the guidewire and the extension wire are both tapered and each have a helically would wire pitched to mate with the respective end of the turnbuckle thus effecting a matching bolt.

The tip of the extension wire is inserted into the end of the outer body having the left-handed helically wound wire to engage the left-handed helical groove. The tip of the guidewire is inserted into the end of the outer body having the right-handed helically wound wire and then into the right-handed helical groove. The turnbuckle nut is then rotated clockwise, when viewed distally, causing the tip of the extension wire to pass along the left-handed helical groove until it reaches the end of the left-handed helical groove while, at the same time, causing the tip of the guidewire to pass along the right handed groove until it reaches the end of the right handed groove. Thus, the tip of the guidewire and the tip of the extension wire will preferably meet inside the turnbuckle nut at the same time that the tapers on the guidewire and extension wire engage the respective ends of the turnbuckle nut.

When not in use, the guidewire extension system may be easily disengaged by rotating the outer body in a counterclockwise direction, when viewed distally, so that the tip of the extension wire will pass along the left-handed groove until it reaches the opening of the outer body and can be removed from the left-handed groove and so that the tip of the guidewire will pass along the right handed groove until it reaches the other opening of the outer body and can be removed from the right-handed groove.

In another preferred embodiment of the present invention, the turnbuckle nut may be permanently attached to the extension wire. In this embodiment, the extension wire is tapered at its connection end and has an extended tip extension core having a smaller diameter than either the extension wire or the extension wire's bolt. The extension wire's bolt is engaged into the respective matching turnbuckle groove. The turnbuckle nut is then permanently secured on the extension core by crimping the outer body around the extension core. The outer turnbuckle nut body can still rotate around the extension core, but the crimp prevents the threads on the turnbuckle nut from completely disengaging from the extension core. The guidewire is connected to the extension wire by inserting the tip of the guidewire into the other end of the outer body and inserting the right-handed, helically wound wire on the extension core into the right-handed, helical groove. The turnbuckle nut is then rotated clockwise, when viewed distally, causing the bolt of the guidewire to engage the right-handed helically wound wire. Once the ends of both guide and extension wires meet and engage the respective ends of the turnbuckle, and after the turnbuckle is rotated sufficiently to fully effect a mechanical connection, the link is stable and does not flex any differently than the guidewire to which it is attached.

It should be noted that the left-handed helically wound wires or left-handed grooves may be substituted by right-handed helically wound wires and right-handed grooves. In those cases, the right-handed helically wound wires and grooves would be substituted by left-handed helically wound wires and grooves and the turnbuckle nut would be rotated counterclockwise, when viewed distally, to connect the guidewire and extension wires.

Other objects, features, and advantages of the invention will become apparent from a consideration of the following detailed description and from the accompanying drawings.

BRIEF DESCRIPTION OF THE DRAWINGS

FIG. 1 is a longitudinal and partial cross-sectional view of a guidewire extension system according to one form of the present invention with the extension wire and guidewire disengaged from the turnbuckle nut;

FIG. 2 is a longitudinal cross-sectional view of the guidewire and extension wire of FIG. 1 engaged with the turnbuckle nut;

FIG. 3 is a side elevation and partial cross-sectional view of an extension wire and connector combination showing the extension wire engaged to the turnbuckle nut with the outer body of the turnbuckle crimped around the extension core of the extension wire; and FIG. 4 is an elevational and segmented view of the end portion of the extension wire, the extension core and the left-handed helically wound wire formed to adhere to the extension core.

DETAILED DESCRIPTION OF THE PREFERRED EMBODIMENTS

As shown in the exemplary drawings, a guidewire extension system is shown which permits easy assembly without the twisting of the guidewire or extension wire, which is easy to manipulate, has a uniform outer diameter, and provides relatively uniform flexibility and pushability through the connector. In accordance with one aspect of the present invention, the guidewire extension system 10 includes a tubular outer body 12, a right-handed helically wound wire 14, and a left-handed helically wound wire 16 forming a turnbuckle nut 43, and a guidewire 18 and an extension wire 20 to be coupled together by the turnbuckle nut (FIG. 1).

The tubular outer body 12 of the connector, which is preferably made of stainless steel, has an opening at each end 22, 24 and a cavity 26 extending longitudinally within the outer body. The wall 28 of the outer body may be tapered at each open end of the outer body to provide a mating surface for the extension and guidewires. Alternatively, the ends of the body may be formed square for ease of manufacture while still allowing solid engagement between the ends of the body and the extension and guidewires.

The right-handed helically wound wire 14 and the left-handed helically wound wire 16 which forms the means by which the extension and guidewires are threadably engaged with the turnbuckle nut 43 are both located within the cavity 26 of the outer body 12 to engage and retain mating portions of the extension and guidewires. The right-handed helically wound wire 14 is preferably brazed to the interior of the tubular outer body on one side of a midpoint of the tubular outer body. The left-handed helically wound wire 16 is preferably brazed to the interior of the tubular outer body on the other side of the midpoint of the tubular outer body. The helically wound wires may also be attached to the interiors of the tubular outer body by welding, soldering, adhesives, frictional engagement or other suitable means. The helically wound wires define a right-handed helical groove 38 and a left-handed helical groove 40 along the inside of the wall of the outer body.

Alternatively, helical grooves may be formed on the inside wall of the tubular outer body by a series of divots formed into the outside of the tubular outer body to create a series of bumps within the inside of the tubular outer body. Further, threads may be formed within the tubular outer body by other means such as roll forming, by mechanical or electric swaging, by machining or by molding (from powder explosion or various conventional molding techniques).

The right-handed helically wound wire 14 and the left-handed helically wound wire 16 are set back from the respective ends of the outer body. The combination of the outer body and the helically wound wires within the outer body form the turnbuckle nut 43 for joining the extension wire and the guidewire. The design of the turnbuckle nut having the helically wound wires is simpler to manufacture than a threaded turnbuckle nut due to the small diameter (0.014 inch) of the outer body. The wire material is preferably 0.001 by 0.006 inch flat stainless steel ribbon wire, and has a pitch when formed in the tubular body of 0.0140 plus or minus 0.0005 inch.

The guidewire 18 and extension wire 20 are preferably constructed of stainless steel and have a diameter of 0.0140 inch. The ends of the guidewire 18 and the extension wire 20 have connection end portions, 44 and 46, respectively. The connection ends of the guidewire and the extension wire preferably are both tapered, at 48 and 50, respectively, and each, in the preferred embodiment, have an enlarged tip, 52 and 54, respectively. The tips may be flattened or otherwise formed to engage the turnbuckle nut. As shown in FIGS. 1 and 2, the flattened tips of the guidewire and the extension wires act as wing style bolts sized to be threaded into the helical grooves 38 and 40 of the turnbuckle nut 43. This design of the extension wire 20 and guidewire 18 is simple to manufacture and provides a simple connection mechanism for the guidewire and extension wire.

The turnbuckle nut 43 connects the guidewire 18 to the extension wire 20 without having to rotate the guidewire 18 or the extension wire 20. The flattened tip 54 of the extension wire is inserted into the end 22 of the outer body 12 having the left-handed helically wound wire 16 and then into the left-handed helical groove 40. The flattened tip 52 of the guidewire is inserted into the end 24 of the outer body having the right-handed helically wound wire 14 and then into the right-handed helical groove 38. The left-handed helically wound wire and the right-handed helically wound wire are spaced far enough from the ends of the outer body to minimize the possibility of kinking or fracture of the ends of the guidewire and extension wire if a side force is applied near the turnbuckle nut. The turnbuckle nut 43 is then rotated clockwise (see arrow in FIG. 2) causing the flattened tip 54 of the extension wire to pass along the left-handed helical groove 40 until it reaches the end of the left-handed helical groove while, at the same time, causing the flattened tip 52 of the guidewire to pass along the right-handed helical groove 38 until it reaches the end of the right-handed helical groove. The pitch of the left-handed and right-handed helically wound wires are preferably twice the longitudinal thickness of the flattened tips of the extension wire and the guidewire, sufficient to allow the flattened tip of the guidewire and extension wire to pass through the left-handed and right-handed grooves. Thus, the flattened tip of the guidewire and the flattened tip of the extension wire will meet at the ends of the wire and the right-handed helically wound wire. Further, when fully engaged, the guidewire and the extension wire will engage and bear against the outside edge of the wall of the turnbuckle to minimize the longitudinal and transverse play between the guidewire, extension wire and turnbuckle and to create a frictional contact to lock the guidewire and extension wire within the turnbuckle nut. Such engagement provides a connection having the same pushability and flexibility as the guidewire.

When not in use, the guidewire extension system may be easily disengaged by rotating the turnbuckle nut 43 in a counterclockwise direction, when viewed distally, to cause the flattened tip 52 of the guidewire 18 to pass along the left-handed groove 38 until it reaches the opening of the outer body 24 to be removed from the left-handed groove and to cause the flattened tip 54 of the extension wire 20 to pass along the right hand groove 40 until it reaches the other opening 22 of the outer body to be removed from the right-handed groove.

In a further embodiment of the present invention, the extension wire and guidewire may include helically arranged threads instead of having flattened tips. In this embodiment, the extension wire and guidewire are preferably tapered 56 at their connection ends and have a reduced diameter extension core 58. (See FIG. 4 for the extension wire. The guidewire is not shown in FIGS. 3 and 4, though it should be understood as described herein that the guidewire tip is formed similar to the extension wire tip but with opposite threads.) A left-handed helically wound wire 62, having a preferred pitch of 0.0140 inch, the same as the left-handed helically wound wire of the turnbuckle nut 43, is brazed to the extension core of the extension wire (see FIG. 4). A right-handed helically wound wire, having a preferred pitch of 0.014 inch, the same as the right-handed helically wound wire of the turnbuckle nut, is also brazed to the extension core of the guidewire. The extension wire and guidewire are connected together by inserting the extension core of the extension wire into the end 22 of the outer body 12 and by inserting the extension core of the guidewire into the end 24 of the outer body. The left-handed helically wound wire 62 of the extension wire is then inserted into the left-handed groove and the right-handed helically wound wire of the guidewire is then inserted into the right-handed groove of the turnbuckle nut and the turnbuckle nut is rotated clockwise to pull together the extension wire and guidewire until the tapers of the guidewire and extension wire abut and bear against the outside edges of the wall of the turnbuckle nut. The tapers of the extension wire and guidewire allow frictional contact with the outside edges of the turnbuckle nut providing a mechanical lock between the three parts and providing a connection having the same pushability and flexibility as the guidewire.

In a further embodiment of the present invention, the extension wire may include helically arranged threads and the turnbuckle nut may be permanently mounted to the connection end 56 of the extension wire 20 (see FIG. 3). One advantage of mounting the connector to the extension wire is that the extension wire/outer body combination may be maintained in one sterile package during the surgical procedure, the sterile package being opened only if the extension wire is need during the operation.

In this embodiment, the extension wire is preferably tapered 56 at its connection end and has a reduced diameter extension core 58. A left-handed helically wound wire 62, having a preferred pitch of 0.0140 inch, the same as the left-handed helically wound wire of the turnbuckle, is brazed to the extension core (see FIG. 4). The extension core 58 is engaged with the turnbuckle nut by inserting the extension core into the end 22 of the outer body 12. The left-handed helically wound wire 62 is then inserted into the left-handed groove 40 and the turnbuckle nut is rotated clockwise. The turnbuckle nut is rotated a sufficient amount until it reaches a point where, if the guidewire is inserted into the turnbuckle nut and the nut turned to thread the nut onto both of the wires at the same time, the ends of the outer body will firmly engage both of the tapered walls of the extension wire and the guidewire (see FIG. 3).

The turnbuckle nut is permanently mounted on the extension core 58 by crimping 64 the outer body around the extension core. The outer body can still rotate around the extension core before it is connected to a guidewire, but the extension is preferably packaged so that the outer body cannot rotate and move longitudinally along the extension core while still in the package. The crimp prevents the threads on the turnbuckle nut from completely disengaging from the extension core during assembly to the guidewire. The guidewire in this embodiment also has preferably a reduced diameter core and has a right-handed helically wound wire brazed to its core in a manner similar to the connection end of the extension wire.

In these additional embodiments, the helically wound wires may also be attached to the extension core of the guidewire and extension wire by welding, soldering, adhesives, or frictional engagements, for example. Additionally, engagement may also be accomplished by forming threads or other engagement means on the respective extrusion cores by roll forming or other conventional means.

The guidewire 18 is connected to the extension wire 20 by inserting the tip of the guidewire into the right-handed helical groove 38 and rotating the turnbuckle nut 43 clockwise until the end of the outer body engages and bears against the taper on the guidewire end portion providing a mechanical lock. At the same time, the opposite end of the turnbuckle nut engages the taper on the extension wire, thereby providing a connection that has the same pushability and flexibility as the guidewire.

The turnbuckle nut, guidewire, and extension wire connection provides many advantages. Connecting the guidewire and the extension wire by the use of the turnbuckle nut is advantageous since there is no potential for disengagement of the extension wire from the guidewire during normal use and since the connection is made without rotating the guidewire or the extension wire. The attachment juncture (the turnbuckle nut with the guidewire and extension wires connected) is sufficiently strong to produce approximately the same flexibility and pushability as the guidewire and extension wire. Further, the attachment juncture provides a unitized system that has a smooth, substantially continuous outer diameter of the extension wire, guidewire, and outer body. The smooth, continuous outer diameter of the attachment structure prevents snagging of the catheter and permits use of a catheter having the minimum diameter necessary to achieve the desired results.

While a particular form of the invention has been illustrated and described, it will be apparent that various modifications can be made without departing from the spirit and scope of the invention. Thus, by way of example and not of limitation, the turnbuckle may be a turnbuckle bolt rather than a turnbuckle nut, having a threaded interior with the connection ends of the extension wire and guidewire having a nut at its end manufactured by shaping the metal of the guidewire and extension wire. Further, the left-handed helically wound wires, and left-handed grooves may be substituted by right-handed helically wound wires and grooves. In these cases, the right-handed helically wound wires and grooves would be substituted by left-handed helically wound wires and grooves and the turnbuckle nut would be rotated counterclockwise, when viewed distally, to connect the guidewire and extension wires. Accordingly, it is not intended that the invention be limited to the specific embodiment disclosed in the drawings and described in detail hereinabove.

We claim:

1. A flexible small diameter connector for connecting a flexible extension wire to a flexible guidewire for the purpose of exchanging human vessel tracking devices, the connector comprising:
   an elongated flexible outer body extending longitudinally;
   said body including a wall defining an opening in each end of the body and defining a cavity extending longitudinally within the body;
   a guidewire retention element located within the cavity of the outer body for mechanically locking an end of said guide wire wherein the guidewire retention is effected by rotating the outer body; and
   an extension wire retention element located within the cavity of the outer body for mechanically locking an end of said extension wire wherein the extension wire retention is effected by rotating the outer body.

2. The connector of claim 1 wherein the outer body includes a tubular member for accepting an end of a guidewire and for accepting an end of an extension wire.

3. The connector of claim 2 wherein the guidewire retention element and the extension wire retention element include helically wound wires in the outer body.

4. The connector of claim 3 wherein the guidewire retention element is a right-handed helically wound element and the entension wire retention element is a left-handed helically wound element.

5. The connector of claim 3 wherein the guidewire retention element is a left-handed helically wound element and the extension wire retention element is a right-handed helically wound element.

6. The connector of claim 3 wherein the helical guidewire retention element and the helical extension wire retention element are brazed to the wall of the outer tube.

7. The connector of claim 1 wherein the inside portion of the wall of the outer body is tapered at each end to accept the end of an extension wire and the end of a guidewire.

8. The connector of claim 1 wherein when a reduced diameter connection end portion of said extension wire is mechanically locked in one end of the outer body and a reduced diameter connection end portion of said guidewire is mechanically locked in the other end of the outer body, the outer diameters of the extension wire, the connector and the guidewire are substantially the same.

9. The connector of claim 1 wherein the guidewire retention element and the extension wire retention element comprise helical threads formed on the wall of the outer body.

10. The connector of claim 9 wherein the guidewire retention element comprises right-handed helical threads and the extension wire retention element comprises left-handed helical threads.

11. The connector of claim 9 wherein the guidewire retention element comprises left-handed helical threads and the extension wire retention element comprises right-handed helical threads.

12. A flexible extension wire for connecting to a flexible guidewire for use in exchanging human vessel tracking devices, the extension wire comprising:
   a flexible extension element; and
   a flexible mechanical coupling at one end of the extension element, the mechanical coupling including:
   a flexible tubular outer body extending longitudinally from the extension element, the tubular outer body having a wall defining an inside cavity and opening at each end of the outer body,
   a left-handed wound helical wire formed to adhere to the inside wall of the tubular outer body for mechanically locking an end of the extension element engaging the helical element, and
   a guidewire retention element for mechanically locking an end of a guidewire.

13. The extension wire of claim 12 wherein the guidewire retention element includes a helically wound wire.

14. The extension wire of claim 13 wherein the guidewire retention element is a right-handed wound element.

15. The extension wire of claim 12 wherein the guidewire retention element is a right-handed helically wound wire and the guidewire retention element is a left-handed helically wound wire.

16. The extension wire of claim 12 wherein the guidewire retention element is brazed to the inside wall of the tubular outer body.

17. The extension wire of claim 12 wherein the inside portion of the wall is tapered at the end of the outer body to accept the end of a guidewire.

18. The extension wire of claim 12 wherein when a guidewire is retained in the end of the outer body, the outer diameters of the extension wire and the guidewire are substantially the same.

19. The extension wire of claim 12 wherein the extension element has a connection end, the connection end being tapered to an extension core of a smaller diameter than the extension element, the extension core having a left-hand helically wound wire formed to adhere to its exterior wherein when the extension core is engaged to the helically wound wire of the outer body, the outer body is crimped to the extension core.

20. The extension wire of claim 12 wherein the guidewire retention element comprises helical threads formed on the wall of the tubular outer body.

21. The extension wire of claim 20 wherein the guidewire retention element comprises right-handed helical threads.

22. A guidewire extension system for use in exchanging human vessel tracking devices, the guidewire extension system comprising:
   an elongate flexible tubular outer body extending longitudinally, the outer body having a wall defining an outer cavity and openings at each end of the outer body;
   a flexible guidewire having a connection end;
   a flexible extension wire having a connection end;
   a guidewire retention element located within the cavity of the tubular outer body for mechanically locking an end of the guidewire; and
   an extension wire retention element located within the cavity of the tubular outer body for mechanically locking an end of the extension wire;
   wherein both the connection end of the guidewire is engaged to the guidewire retention element and the connection end of the extension wire is engaged to the extension wire retention element by rotating the outer body.

23. The guidewire extension system of claim 22 wherein the guidewire retention element is a right-handed helically wound wire defining a right-handed helical groove and the extension wire retention element is a left-handed helically wound wire defining a left-handed helical groove, and the connection end of the guidewire is tapered and has a flattened tip and the connection end of the extension wire is tapered and has a flattened tip, and the guidewire is connected to the outer body and the extension wire is connected to the outer body by engaging the flattened tip of the guidewire to the right-handed helical groove and by engaging the flattened tip of the extension wire to the left-handed helical groove and then rotating the outer body in a clockwise direction causing the flattened tip of the guidewire to pass along the right-handed helical groove and causing the flattened tip of the extension wire to pass along the left-handed helical groove.

24. The guidewire extension system of claim 22 wherein the guidewire retention element is a left-handed helically wound wire defining a left-handed helically wound wire defining a left-handed helical groove and the extension wire retention element is a right-handed helically wound wire defining a right-handed helical groove and wherein the connection end of the guidewire is tapered and has a flattened tip and the connector end of the extension has a flattened tip, and the guidewire is connected to the outer body and the extension wire is connected to the outer body by engaging the flattened tip of the guidewire to the left-handed helical groove and by engaging the flattened tip of the extension wire to the right-handed helical groove and then rotating the outer body in a counter-clockwise direction causing the flattened tip of the guidewire to pass along the left-handed helical groove and causing the flattened tip of the extension wire to pass along the right-handed helical groove.

25. The guidewire extension system of claim 22 wherein the inside portion of the wall is tapered at each end of the outer body to accept the connection end of the extension wire and the connection end of the guidewire.

26. The guidewire extension system of claim 22 wherein when the extension wire is mechanically locked in one end of the outer body and the guidewire is mechanically locked in the other end of the outer body, the outer diameter of the extension wire, the connector and the guidewire are substantially the same.

27. A connector for connecting an extension wire to a guidewire for use in exchanging vessel tracking devices, the connector comprising:
 an outer body extending longitudinally;
 a wall defining an opening in each end of the body and defining a cavity extending longitudinally within the body;
 a guidewire retention element located within the cavity of the outer body for retaining an end of a guidewire wherein the guidewire retention is effected by rotating the outer body;
 a extension wire retention element located within the cavity of the outer body for retaining an end of an extension wire wherein the extension wire retention is effected by rotating the outer body;
 an extension wire having a tapered end connection portion and retained by the extension wire retention element; and
 a guidewire having a tapered end connection portion and retained by the guidewire retention element;
 wherein the tapered end connection portions of the extension wire and guidewire frictionally engage and thereby mechanically lock the end of the outer body wall when the outer body and the extension wire and the guidewire are fully engaged.

28. The connector of claim 27 wherein the guidewire retention element and the extension wire retention element comprise helical threads formed on the wall of the outer body.

29. A method of connecting a flexible small diameter extension wire to a flexible small diameter guidewire for the purpose of exchanging human vessel tracking devices, comprising:
 coupling the extension wire to a connector;
 coupling the guidewire to the connector;
 rotating the connector to simultaneously pull the guidewire and extension wire together and to mechanically lock the extension wire and guidewire together; and
 providing said connector and coupled portions of said wires with a flexibility such that with said wires connected to said connector a flexibility at said connector is provided which is substantially the same as the flexibility of said wires.

30. The method of claim 29 wherein the connector comprises a tubular outer body having a right-handed helically wound wire and a left-handed helically wound wire located within the outer body and wherein the guidewire and extension wires have a flattened tip at their ends.

31. The method of claim 29 wherein the connector comprises a tubular outer body having right-handed helical threads and left-handed helical threads formed on the outer body and wherein the guidewire and extension wires have a flattened tip at their ends.

32. A flexible extension wire for connecting to a flexible guidewire for use in exchanging human vessel tracking devices, the extension wire comprising:
 a flexible extension element; and
 a flexible mechanical coupling at one end of the extension element, the mechanical coupling including:
 an elongate flexible tubular outer body extending longitudinally from the extension element, the tubular outer body having a wall defining an inside cavity and openings at each end of the outer body,
 left-handed helical threads formed on the inside wall of the tubular outer body for mechanically locking an end of the extension element engaging the helical groove, and
 a guidewire retention element for mechanically locking an end of a guidewire.

33. The extension wire of claim 32 wherein the guidewire retention element comprises helical threads formed on the wall of the tubular outer body.

34. The extension wire of claim 32 wherein the extension element has a connection end, the connection end being tapered to an extension core of a smaller diameter than the extension element, the extension core having left-handed threads formed thereon for engaging the helical threads of the outer body, wherein the outer body is crimped to the extension core.

35. A flexible coupling structure for securing together a small diameter flexible extension wire and a flexible guide wire of like diameter and transmitting both tension and pushing forces between the wires, said coupling structure comprising:
 each of said guide wire and said extension wire including a respective elongate flexible connection end portion of reduced diameter, said connection end portions each including a tapering part defining a tapering surface section adjacent the remainder of each wire and said connection end portions also terminating at a respective tip surface, each of said connection end portions including a respective tip portion proximate to said tip surface, and said tip portions of each wire defining respective thread-engaging means of opposite hand;

an elongate flexible tubular body having a circumferential wall defining an outer diameter substantially like said guide wire and said extension wire, said wall defining opposite end openings to said body and a cavity extending between said openings, said tubular body at a central part thereof spaced from said end openings including thread-defining means having respective portions of opposite hand extending longitudinally of said body for threadably engaging said thread-engaging means of both said guide wire and said extension wire;

whereby said guide wire and said extension wire at said connection end portions thereof are each receivable into said tubular body to threadably engage said thread-engaging means of each with said thread-defining means of said body so that rotation of said body relative both said guide wire and extension wire simultaneously draws the connection end portions of the wires together to abut said tip surfaces with one another and frictionally engages said tapering surface sections of each connection end portion with said body at a respective end opening thereof, and said body and connection end portions together having a flexibility approximating the flexibility of said guide wire and extension wire.

36. The coupling structure of claim 35 wherein said end connection portions include an enlarged tip part defining said tip surface, and said thread-engaging means includes said enlarged tip parts being configured to threadably engage with said body at said thread-defining means thereof.

37. The coupling structure of claim 36 wherein said end connection portions include an elongate cylinderical portion of reduced diameter, and said thread-engaging means includes a helix of wire wound about and secured to said cylindrical portion.

38. The coupling structure of claim 35 wherein said body includes intermediate said central thread-defining portion and one end of said body, means for capturing a respective thread-engaging portion of one of said guide wire and extension wire therein, whereby said tubular body is received on said end connection portion of the respective one of said guide wire and said extension wire and permanently retained with said one respective wire by said capturing means.

39. The coupling structure of claim 38 wherein said means for capturing includes said body wall defining a protrusion extending radially inwardly thereof into said cavity and toward but short of said end connection portion, said protrusion being engageable by said thread-engaging means of said one wire for preventing said wire from withdrawal from said cavity.

40. The coupling structure of claim 39 wherein said protrusion is annular to define a collar capturing said tip portion in said cavity.

41. The coupling structure of claim 35 wherein said thread-defining means of said tubular body includes a helix of wire in said cavity and secured to said wall.

* * * * *